(12) United States Patent
Dixon

(10) Patent No.: US 7,295,689 B2
(45) Date of Patent: *Nov. 13, 2007

(54) SYSTEM AND METHOD FOR REAL-TIME PROCESSING AND DISPLAY OF DIGITAL MEDICAL IMAGES

(75) Inventor: Walter V. Dixon, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 834 days.

This patent is subject to a terminal disclaimer.

(21) Appl. No.: 10/604,293

(22) Filed: Jul. 9, 2003

(65) Prior Publication Data

US 2005/0008203 A1     Jan. 13, 2005

(51) Int. Cl.
*G06K 9/00* (2006.01)
(52) U.S. Cl. ..................... 382/128; 382/274
(58) Field of Classification Search ........... 382/128, 382/132, 274, 307; 378/98, 98.7, 98.12
See application file for complete search history.

(56) References Cited

U.S. PATENT DOCUMENTS

| | | | |
|---|---|---|---|
| 5,053,770 A * | 10/1991 | Mayer et al. ............... 341/118 |
| 5,177,697 A * | 1/1993 | Schanen et al. ....... 364/571.04 |
| 5,220,589 A * | 6/1993 | Gard ............................ 378/19 |
| 5,422,805 A | 6/1995 | McIntyre et al. ............ 364/757 |
| 5,519,441 A | 5/1996 | Gusmano et al. ............ 348/207 |
| 5,594,854 A | 1/1997 | Baldwin et al. ............. 395/141 |
| 5,684,728 A | 11/1997 | Okayama et al. ......... 364/736.5 |
| 5,874,909 A | 2/1999 | Soenen et al. .............. 341/141 |
| 6,314,443 B1 | 11/2001 | Seal ............................ 708/552 |
| 6,504,895 B1 | 1/2003 | Dixon et al. .................. 378/19 |
| 2003/0002725 A1* | 1/2003 | Dixon et al. ................ 382/132 |

* cited by examiner

*Primary Examiner*—Andrew W. Johns
(74) *Attorney, Agent, or Firm*—Fletcher Yoder

(57) ABSTRACT

A method of processing image data of a scanned object includes performing, in integer format, a pixel offset correction on the image data using unsigned saturation arithmetic to produce an image in integer format having negative value pixels clipped to a value of zero. The resulting pixels are converted to floating point format and are multiplied by a positive floating point gain factor. The resulting pixels are further converted to integer format and clamped to a maximum value using saturation arithmetic. Non-functional pixel correction is performed in integer format, and the resulting pixel values are clamped to a maximum value using saturation arithmetic. The resulting pixel value is mapped in integer format to a palette index using a lookup table to establish an output pixel intensity having one of a plurality of intensity levels.

19 Claims, 2 Drawing Sheets

SYSTEM AND METHOD FOR REAL-TIME PROCESSING AND DISPLAY OF DIGITAL MEDICAL IMAGES

BACKGROUND OF THE INVENTION

The present disclosure relates generally to processing of imaging system data and, more particularly, to a system and method for processing medical images in real time using a commercially available, off the shelf processor(s).

Medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems and nuclear medicine systems. In many instances, these modalities complement one another and offer the physician a range of techniques for imaging particular types of tissue, organs, physiological systems, and so forth. Health care institutions often dispose of several such imaging systems at a single or multiple facilities, permitting its physicians to draw upon such resources as required particular patient needs.

Modern medical diagnostic systems typically include circuitry for acquiring image data and for transforming the data into a useable form, which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

For example, radiography is the technique of producing an image of any opaque specimen by the penetration of radiation, such as gamma rays, x-rays, neutrons, or charged particles, for example. When a beam of radiation is transmitted through any heterogeneous object, the radiation is differentially absorbed depending upon varying object thickness, density, and chemical composition. The emerging energy from the object forms a radiographic image, which may then be realized on an image detection medium, such as a radiation sensitive detector having an array of elements that generate a signal output depending on the level of radiation absorbed, the detector signal output being converted into a voltage for exciting display pixels. As radiography is a non-destructive technique for testing the gross internal structure of an object, it is conventionally used in both medical and industrial applications. More specifically, radiography is used to detect medical conditions such as tuberculosis and bone fractures, as well as to non-destructively detect manufacturing imperfections in materials such as cracks, voids, and porosity.

Regardless of the imaging modality, the conventional processing techniques are generally implemented with application specific processors that are configured for specific system components. This design makes such processing systems expensive to purchase and operate. Accordingly, it is desirable to be able to process data from medical imaging systems at a lower cost such as through commercial off the shelf hardware and/or software.

BRIEF DESCRIPTION OF THE INVENTION

The above discussed and other drawbacks and deficiencies of the prior art are overcome or alleviated by a method of processing image data of a scanned object. In an exemplary embodiment, the method includes performing, in integer format, a pixel offset correction on the image data using unsigned saturation arithmetic to produce an image in integer format having negative value pixels clipped to a value of zero. The resulting pixels are converted to floating point format and are multiplied by a positive floating point gain factor. The resulting pixels are further converted to integer format and clamped to a maximum value using saturation arithmetic. Non-functional pixel correction is performed in integer format, and the resulting pixel values are clamped to a maximum value using saturation arithmetic. The resulting pixel value is mapped in integer format to a palette index using a lookup table to establish an output pixel intensity having one of a plurality of intensity levels.

In another aspect, a computer program article for processing image data of scanned object includes a storage medium, readable by a commercial off the shelf processing circuit. The storage medium includes instructions for execution by the processing circuit for performing, in integer format, a pixel offset correction on the image data using a dark image subtraction and saturation arithmetic to produce an image in integer format having negative value pixels clipped to a value of zero. The resulting pixels are converted to floating point format and are multiplied by a positive floating point gain factor. The resulting pixels are further converted to integer format and clamped to a maximum value using saturation arithmetic. Non-functional pixel correction is performed in integer format, and the resulting pixel values are clamped to a maximum value using saturation arithmetic. The resulting pixel value is mapped in integer format to a palette index using a lookup table to establish an output pixel intensity having one of a plurality of intensity levels. The mapped image data is filtered to enhance feature recognition within the thickness range of the scanned object, and the filtered image data is displayed in real-time at a frame rate of equal to or greater than 30 million pixels per second.

In still another aspect, a medical imaging system includes an image device adapted to acquire and output image data, an imaging system controller in communication with the image device, the imaging system controller configured to receive commands from a computer, and a display device for displaying the image data. The computer further includes a processor programmed for performing, in integer format, a pixel offset correction on the image data using a dark image subtraction and saturation arithmetic to produce an image in integer format having negative value pixels clipped to a value of zero. The resulting pixels are converted to floating point format and are multiplied by a positive floating point gain factor. The resulting pixels are further converted to integer format and clamped to a maximum value using saturation arithmetic. Non-functional pixel correction is performed in integer format, and the resulting pixel values are clamped to a maximum value using saturation arithmetic. The mapped image data is filtered to enhance feature recognition within the thickness range of the scanned object. The resulting pixel value is mapped in integer format to a palette index using a lookup table to establish an output pixel intensity having one of a plurality of intensity levels, and the filtered image data is displayed in real-time at a frame rate of equal to or greater than 30 million pixels per second on the display device.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a medical imaging system and method that dynamically processes obtained images in real-time using a plurality of one or more commercial off the shelf (COTS) processors having native saturation arithmetic capability. Saturation arithmetic refers to a known processor characteristic where calculations are clipped to a preset range. The specific nature of the clipping depends on whether one performs signed or unsigned arithmetic. Signed saturated subtraction clips the result to the largest negative value that the bit-depth can support, whereas unsigned saturated subtraction clips the result to zero. Furthermore, saturated addition clips the result to the largest positive value that the bit depth can support. For a given bit depth, numerical range depends on whether a quantity is treated as a signed or unsigned value.

While the embodiments described herein depict x-rays generated in a radiographic imaging system as an exemplary type of radiation for radiographic imaging, it will be appreciated that the present invention is also applicable to other radiation types, such as gamma rays, high-frequency sound waves, magnetic fields, neutrons, or charged particles for example. Furthermore, it also applicable to other medical imaging modalities (e.g., CT, MRI, PET), as well as non-medical imaging uses.

Figure 1:
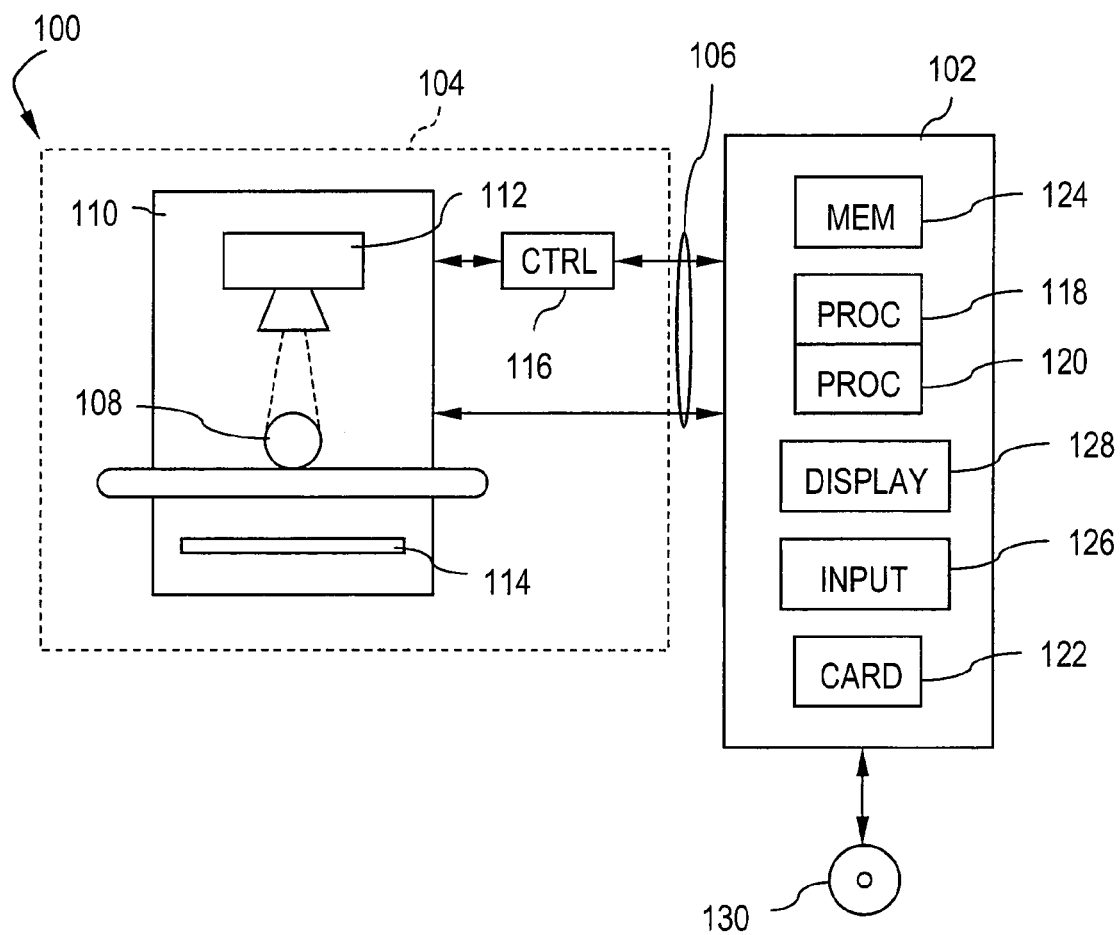
FIG. 1 is an exemplary medical imaging system suitable for implementing an embodiment of the invention.

Referring initially to FIG. 1, there is shown an exemplary embodiment of a radiographic inspection system 100 that includes a computer 102 adapted to be in signal communication with a medical imaging system 104 via a communication bus 106. The imaging system 104 is adapted to acquire and output radiographic image data of a scanned object 108 (e.g., a patient) via an imaging device 110, which includes an x-ray source 112 and image detector 114. The imaging system 104 also includes an imaging system controller 116 that receives control commands from computer 102 and sends control signals to the various components of imaging device 110.

The computer 102 includes one or more processors 118, 120 to execute operations according to a set of instructions provided by installed application software (discussed in further detail hereinafter), a detector interface card 122 (also discussed in further detail hereinafter), at least one memory 124 to store the application software and to store the image data received from image detector 114, an input device 126, and a display device 128. The memory 124 refers to any type and number of memory chips, magnetic storage disks, optical storage disks, mass storage devices, or any other storage device suitable for retaining information. The input device 126 may be, for example, a keyboard, a mouse, a pointing device, a touch sensitive screen device, a tablet, a read/write drive for a magnetic disk, a read/write drive for an optical disk, a read/write drive for any other input medium, an input port for a communication link (electrical or optical), a wireless receiver, or any combination thereof.

In addition, the display device 128 may be a CRT (cathode ray tube) screen or any other suitable display device for displaying text, graphics, and a graphical user interface, for example. The detector interface card 122 provides low level control over the image detector, buffers data read out from the image detector, and optionally reorders image pixels to convert from read-out order to display order.

Figure 2:
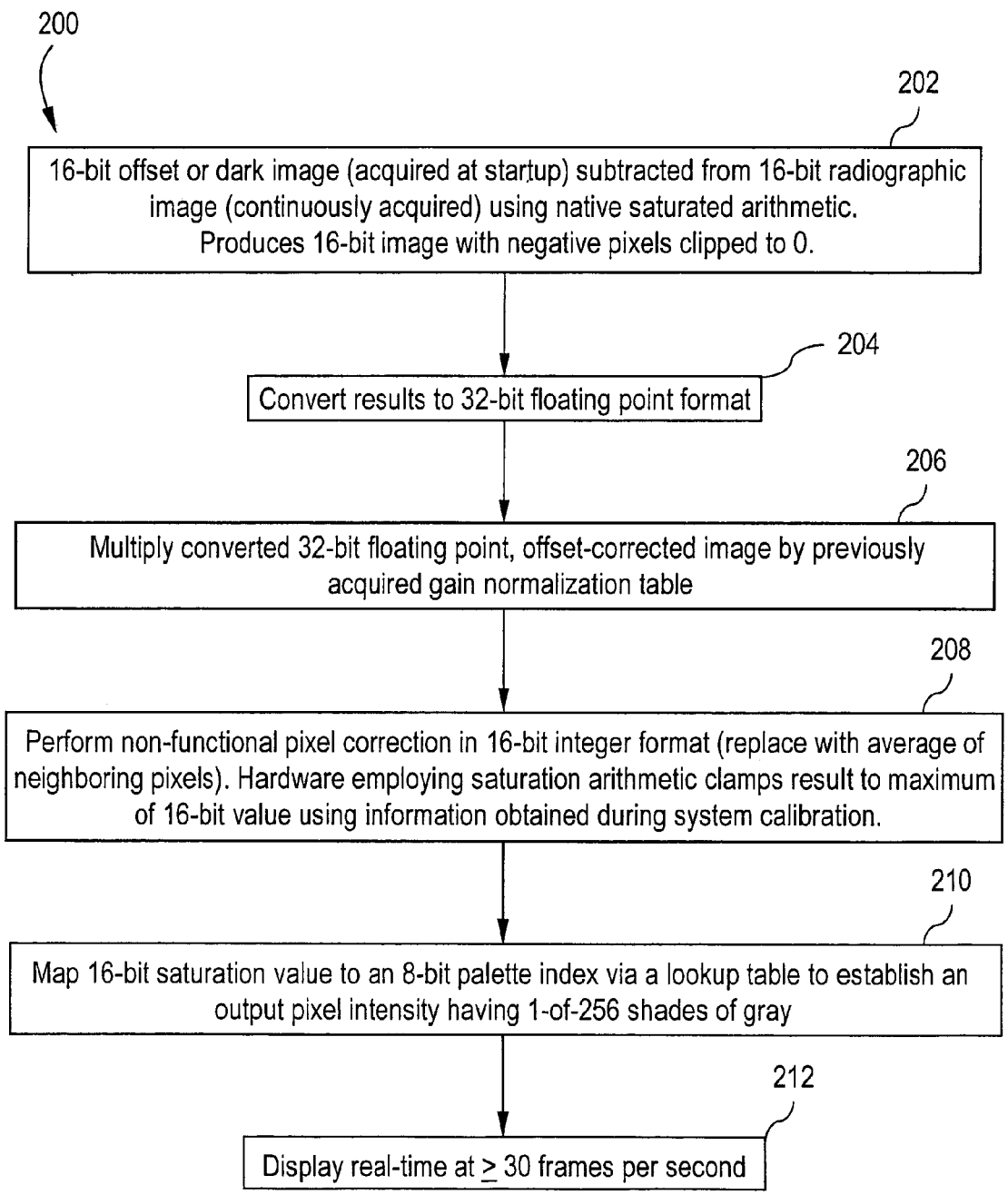
FIG. 2 is an exemplary flow diagram for processing image data using commercial off the shelf hardware/software in accordance with an embodiment of the present invention.

In exemplary embodiments, the processors 118, 120 are a 1.7 GHz or faster Intel Pentium 4 processor and a 2.4 GHZ or faster Intel Xeon processor, respectively, that are programmed to process image data (e.g., radiographic) of scanned object 108 according to a process 200 depicted in FIG. 2. As shown in FIG. 2, process 200 begins at block 202 by performing in 16-bit integer format a pixel offset correction on the 16-bit radiographic image using native saturation arithmetic to produce an image in 16-bit integer format having negative value pixels clipped to a value of zero. In one embodiment, the pixel offset correction involves subtracting dark image (alternatively offset image) pixel values from the radiographic image pixel values, where dark image refers to an image data set acquired in the absence of x-rays and stored at memory 124. As used herein, reference to an operation on a pixel means an operation on the intensity value of the pixel. When system 100 is operating in real-time mode, the 16-bit radiographic images are continuously acquired at imaging device 110, processed by one or more processors 118, 120, and displayed at display 128 at a frame rate equivalent to 30 million pixels per second.

At blocks 204-206, the processor(s) 118, 120 converts the offset corrected image data to a 32-bit floating point number, and multiplies the converted pixels by a 32-bit positive floating point gain factor acquired from a normalization look up table within memory 124. Optionally, this product is weighted with a previously computed product to temporally integrate the noise inherent in the detector. The resulting floating point product is converted to a 16-bit integer value using saturation arithmetic.

Native saturation arithmetic also clamps the 16-bit integers to the maximum value available in 16-bit integer format and to a minimum value of zero, thereby establishing a pixel saturation value that eliminates visual artifacts in the display. The clamped pixel values are clamped to an appropriate 16-bit range and not allowed to wrap. In a preferred embodiment, the operations described in block 202-206 are performed in their entirety on a suitably defined small number/ group of pixels (over multiple iterations) in order to maximize cache performance. The specific number of pixels used in the operations of offset subtraction, gain normalization, optional temporal averaging, and conversion back to integer are optimized according to the size of the cache line supported by the processor.

At block 208, processor(s) 118, 120 performs in 16-bit integer format a non-functional pixel correction by replacing a non-functional pixel with the average pixel intensity value of the neighboring pixels. Other non-functional pixel correction routines may be employed in place of the "average-of-the-neighbors" routine. In one embodiment, a non-functioning pixel is identified during system calibration. The corrected image is then processed using native saturation arithmetic to clamp the pixel values to the maximum value available in 16-bit integer format. The user may in real-time adjust the number of frames that the linear averaging is applied to, thereby obtaining a visually optimal display.

At block 210, the resulting 16-bit corrected pixel value is mapped to display resolution in integer format to an 8-bit palette index via a lookup table at memory 124 to establish an output pixel intensity having one of a plurality (such as 1-of-256, for example) of intensity levels, which in may be displayed as shades of gray. In one embodiment, a single lookup table incorporating both contrast management and gamma correction is used to map the integer resulting pixel to an 8 bit gray scale image suitable for display on a standard monitor. Contrast management can include window/level, histogram equalization, or any other standard image processing technique. Combining the contrast management with the gamma correction avoids the posterization effect produced by using two separate lookup tables. Posterization is a known phenomena in which tiny rectangular regions due to truncation are visible in an image. Finally, as shown in block 212, the resulting image is displayed at a real-time frame rate of equal to or greater than an equivalent of 30 million pixels per second.

The above described process 200 may be embodied in a computer program article 130 (shown in FIG. 1), such as for example a compact disc read-only-memory (CD-ROM), a writeable CD, a rewriteable CD, or any other suitable storage medium that includes program instructions readable by a COTS processor.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of processing image data of a scanned object, the method comprising:
   performing, in integer format, a pixel offset correction on the image data using unsigned saturation arithmetic to produce an image in integer format having negative value pixels clipped to a value of zero;
   converting the resulting pixels to floating point format and multiplying the converted pixels by a positive floating point gain factor;
   converting the resulting pixels to integer format and clamping the converted pixel values to a maximum value using saturation arithmetic;
   performing, in integer format, non-functional pixel correction and clamping the resulting pixel values to a maximum value using saturation arithmetic; and
   mapping in integer format the resulting pixel value to a palette index using a lookup table to establish an output pixel intensity having one of a plurality of intensity levels.

2. The method of claim 1 wherein said mapping in integer format the resulting pixel value to a palette index using a lookup table further comprises:
   using a single lookup table incorporating both contrast management and gamma correction to map the integer resulting pixel to an 8-bit gray scale image, so as to avoid a posterization effect produced by using separate lookup tables.

3. The method of claim 1, wherein:
   said performing a pixel offset correction comprises performing a dark image pixel subtraction from said image data; and
   said mapping the resulting pixel value to a palette index comprises mapping via a lookup table.

4. The method of claim 3, wherein:
   said integer format, said dark image, and the radiographic image are in 16-bit integer format;
   said dark image is acquired in the absence of radiation;
   said floating point format and said gain factor are in 32-bit floating point format;
   said gain factor is acquired from a normalization table;
   said clamped pixel values are clamped to a minimum value of 0;
   said palette index is in 8-bit integer format; and
   said plurality of intensity levels includes at least 256 shades of gray.

5. The method of claim 1, further comprising:
   filtering the mapped image data to enhance feature recognition within the thickness range of the scanned object; and
   displaying the filtered radiographic image in real-time at a frame rate of equal to or greater than 30 million pixels per second.

6. The method of claim 1, wherein the image data is medical image data obtained from scanning a patient.

7. The method of claim 1, wherein:
   said performing a pixel offset correction, said converting the resulting pixels to floating point format and multiplying the converted pixels by a positive floating point gain factor, and said converting the resulting pixels to integer format are implemented through multiple iterations over a defined group of pixels so as to maximize cache performance.

8. A computer program article for processing image data of scanned object, the article comprising:
   a storage medium, readable by a commercial off the shelf processing circuit, including instructions for execution by the processing circuit for:
   performing, in integer format, a pixel offset correction on the image data using a dark image subtraction and saturation arithmetic to produce an image in integer format having negative value pixels clipped to a value of zero;
   converting the resulting pixels to floating point format and multiplying the converted pixels by a gain factor;
   converting the resulting pixels to integer format and clamping the converted pixel values to a maximum value using saturation arithmetic;
   performing, in integer format, non-functional pixel correction and clamping the resulting pixel values to a maximum value using saturation arithmetic;
   mapping in integer format the resulting pixel value to a palette index to establish an output pixel intensity having one of a plurality of intensity levels;
   filtering the mapped image data to enhance feature recognition within the thickness range of the scanned object; and
   displaying the filtered image data in real-time at a frame rate of equal to or greater than 30 million pixels per second.

9. The article of claim 8, wherein:
said performing a pixel offset correction comprises performing a dark image pixel subtraction; said integer format, said dark image, and image data are in 16-bit integer format;
said floating point format and said gain factor are in 32-bit floating point format;
said clamped pixel values are clamped to a 16 bit range and not allowed to wrap;
said palette index is in 8-bit integer format; and
said plurality of intensity levels includes at least 256 shades of gray.

10. The article of claim 9, wherein the storage medium further includes instructions for execution by the processing circuit for:
performing, in floating point format, weighted averaging on the gain-multiplied pixels prior to converting the pixels to integer format and performing the non-functional pixel correction;
wherein said mapping the resulting pixel value to a palette index comprises mapping via a lookup table; and
wherein said gain factor is acquired from a normalization table.

11. The article of claim 8, wherein the image data is medical image data obtained from scanning a patient.

12. The article of claim 8, wherein:
said performing a pixel offset correction, said converting the resulting pixels to floating point format and multiplying the converted pixels by a positive floating point gain factor, and said converting the resulting pixels to integer format are implemented through multiple iterations over a defined group of pixels so as to maximize cache performance.

13. A medical imaging system, comprising:
an image device adapted to acquire and output image data;
an imaging system controller in communication with said image device, said imaging system controller configured to receive commands from a computer; and
a display device for displaying said image data;
said computer further includes a processor programmed for:
performing, in integer format, a pixel offset correction on the image data using saturation arithmetic to produce an image in integer format having negative value pixels clipped to a value of zero;
converting the resulting pixels to floating point format and multiplying the converted pixels by a gain factor;
converting the resulting pixels to integer format and clamping the converted pixel values to a maximum value using saturation arithmetic;
performing, in integer format, non-functional pixel correction and clamping the resulting pixel values to a maximum value using saturation arithmetic;
filtering the mapped image data to enhance feature recognition within the thickness range of the scanned object;
mapping, in integer format, the resulting pixel value to a palette index to establish an output pixel intensity having one of a plurality of intensity levels; and
displaying, on said display device, the filtered image data in real-time at a frame rate of equal to or greater than 30 million pixels per second.

14. The system of claim 13, wherein:
said performing a pixel offset correction comprises performing a dark image pixel subtraction from the image data;
said integer format and the image data are in 16-bit integer format;
said floating point format and said gain factor are in 32-bit floating point format;
said clamped pixel values are clamped to a 16 bit range and not allowed to wrap;
said palette index is in 8-bit integer format; and
said plurality of intensity levels comprises at least 256 shades of gray.

15. The system of claim 14, wherein the processor is further programmed for:
performing, in floating point format, weighted averaging on the gain-multiplied pixels prior to converting the pixels to integer format and performing the non-functional pixel correction;
wherein the mapping the resulting pixel value to a palette index comprises mapping via a lookup table; and
wherein the gain factor is acquired from a normalization table.

16. The system of claim 15, wherein:
said performing a pixel offset correction, said converting the resulting pixels to floating point format and multiplying the converted pixels by a positive floating point gain factor, said performing weighted averaging of the gain multiplied pixels in floating point format, and said converting the resulting pixels to integer format are implemented through multiple iterations over a defined group of pixels so as to maximize cache performance.

17. The system of claim 13, wherein said image device comprises one of: a radiographic device, a computed tomography device and a magnetic resonance device.

18. The system of claim 17, wherein the image data is medical image data obtained from scanning a patient.

19. The system of claim 13, wherein:
said performing a pixel offset correction, said converting the resulting pixels to floating point format and multiplying the converted pixels by a positive floating point gain factor, and said converting the resulting pixels to integer format are implemented through multiple iterations over a defined group of pixels so as to maximize cache performance.

* * * * *